United States Patent [19]

Gohda et al.

[11] Patent Number: 5,004,805
[45] Date of Patent: Apr. 2, 1991

[54] HEPATOCYTE GROWTH FACTOR

[75] Inventors: Eiichi Gohda, 1-51-2-31 Kinkodai; Hirohito Tsubouchi, 1925 Harara-cho, both of Kagoshima-shi, Kagoshima-ken; Hiroyuki Nakayama, Kagoshima; Shuichi Hirono, Kagoshima; Kozo Takahashi, Kagoshima; Shuji Hashimoto, 6-49-3 Murasakibaru; Yasushi Daikuhara, 4-14-10-41 Meiwa, both of Kagoshima-shi, Kagoshima-ken, all of Japan

[73] Assignees: Shuji Hashimoto; Yasushi Daikuhara; Eiichi Gohda; Hirohito Tsubouchi, all of Kagoshima; Mitsubishi Kasei Corporation, Tokyo, all of Japan

[21] Appl. No.: 58,211

[22] Filed: Jun. 4, 1987

[30] Foreign Application Priority Data

Jul. 14, 1986 [JP] Japan ................................ 61-166495

[51] Int. Cl.$^5$ .......................... C07K 7/10; C07K 15/00
[52] U.S. Cl. .................................... 530/399; 530/324; 530/846
[58] Field of Search ................. 424/101; 530/324, 399, 530/846

[56] References Cited

PUBLICATIONS

Nakayama, *Biomedical Research*, 6(4), 231–237 (1985).
Creighton, *Proteins, Structure and Molecular Principles*, W. H. Freeman and Company, N.Y., 1984, pp. 113–114.
Thaler, *Cancer Research*, 45, 2545–2549 (1985).
Russell, *Journal of Cellular Physiology*, 119, 183–192 (1984).
"Control of Hepatocyte Replication by Two Serum Factors", Michalopoulos et al., *Cancer Research*, 44, 4414–4419, Oct. 1984.

*Primary Examiner*—F. T. Moezie
*Attorney, Agent, or Firm*—Oblon, Spivak, McClelland, Maier & Neustadt

[57] ABSTRACT

A hepatocyte growth factor comprising a proteinous substance derived from human blood and showing the following physicochemical properties and physiologic activity:

(i) its molecular weight is estimated to be approximately 76,000 to 92,00 by SDS-PAGE analysis (under non-reductive conditon);
(ii) it possesses HGF activity;
(iii) the HGF activity is inactivated by heat treatment for 10 minutes at 80° C.;
(iv) the HGF activity may be lost by digestion with trypsin or with chymotrypsin; and
(v) it has a high affinity for heparin.

3 Claims, 4 Drawing Sheets

HEPATOCYTE GROWTH FACTOR

This invention relates to a hepatocyte growth factor, hereinafter referred to as HGF, particularly to a new proteinous substance derived from human blood and capable of proliferating the hepatocytes.

DESCRIPTION OF THE BACKGROUND

A liver is a highly differentiated adenogenous organ which plays an important role in the intermediate metabolism of living body, and its function is sustained by hepatic parenchymal cells constituting this organ. In a rat, for example, it is known that even after surgical resection of about two-thirds of the liver the remaining hepatic tissue promptly grows and may be restored to its original size in about 10 days.

Based on the fact, patients suffering from hepatic carcinoma are often treated in such a way that the remaining normal hepatic tissue is allowed to proliferate after a partial hepatectomy.

A lot of researches and investigations have been pursued to elucidate the mechanism of the foregoing proliferation of the liver (hepatic regeneration). According to such studies, it was suggested that some growth promoting factor might appear in the blood of hepatectomized rat, and there have been several reports on the success in a partial purification of the same factor (rat hepatocyte growth factor: rHGF). However, the rHGF preparations reported have diversity with respect to molecular weight and other physicochemical properties, and remain to be clarified in many respects. As yet, there has been no report demonstrating the presence of a similar hepatocyte growth factor in a human blood.

SUMMARY OF THE INVENTION

The present inventors have been intensively engaged in investigating the afore-mentioned hepatocyte growth factor, during which it was first discovered that sera from patients with fulminant hepatitis possessed a high HGF activity (Biomed. Res., 6, 231 (1985)).

It is an object of this invention to isolate and purify the new hepatocyte growth factor present in the blood of patients with the fulminant hepatitis so as to acquire informations with regard to its properties and clinical application.

The present invention provides human hepatocyte growth factor (hHGF) comprising a proteinous substance derived from human blood and showing the following physicochemical properties and physiological activity:

(i) its molecular weight is estimated to be approximately 76,000 to 92,000 by SDS-PAGE analysis (under non-reductive condition);
(ii) it possesses HGF activity;
(iii) the HGF activity is inactivated by heat treatment for 10 minutes at 80° C.;
(iv) the HGF activity may be lost by digestion with trypsin or with chymotrypsin; and
(v) it has a high affinity for heparin.

The afore-mentioned characteristics and other properties of the hHGF according to the invention will be further explained in detail in Examples hereinunder described.

DETAILED DESCRIPTION OF THE PREFERRED EMBODIMENTS

Figure 1:
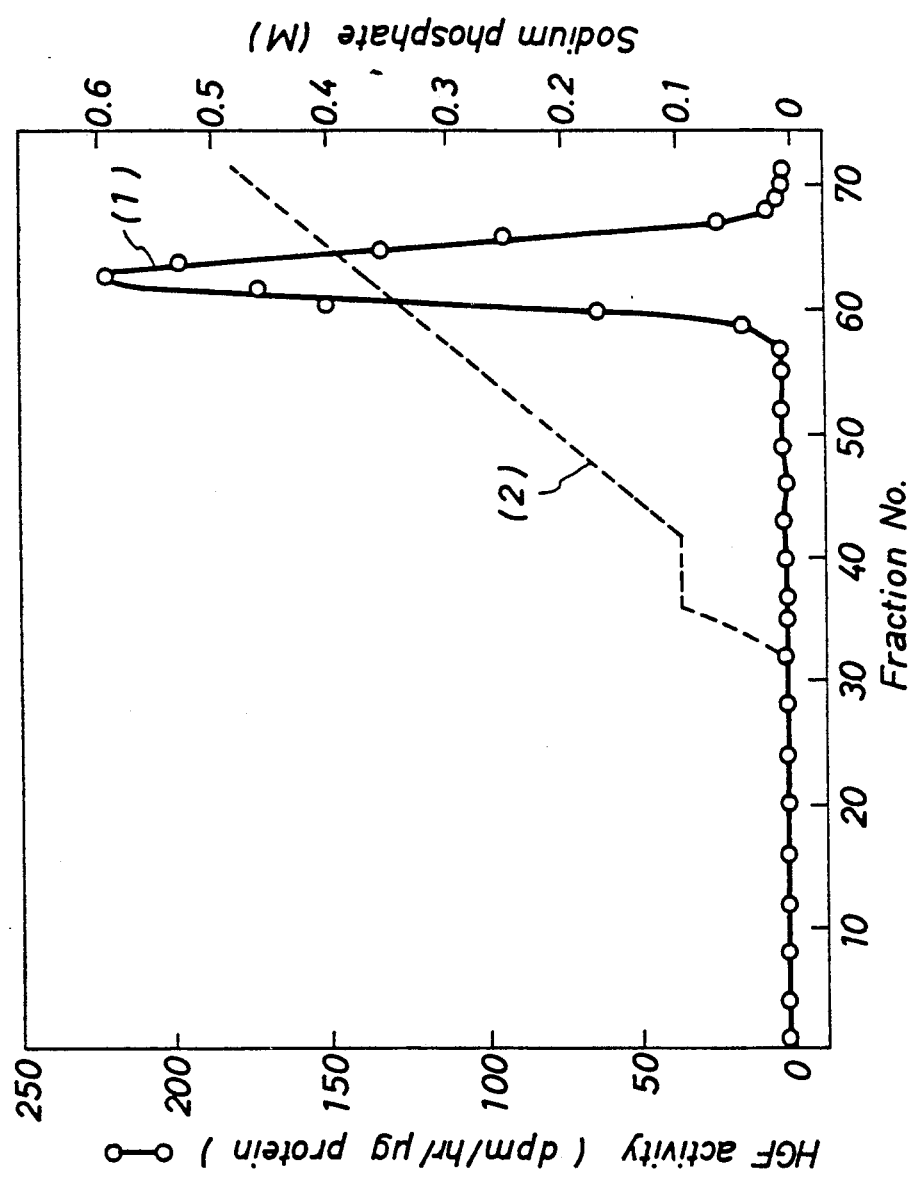
FIG. 1 illustrates the elution pattern of the hHGF of the invention from a hydroxyapatite column.

The hHGF of the present invention is useful as a pharmaceutical preparation for the treatment of hepatic diseases such as acute hepatitis, chronic hepatitis, hepato cirrhosis and fulminant hepatitis and for the postoperative treatment of hepatectomized patients. It may also be served as an antigen for immunological diagnoses of the diseases above. By making use of the hHGF, furthermore, it may be quite readily accomplished to grow and maintain hepatocytes from various species of animals including the human in vitro in the presence of the hHGF, and those hepatocytes grown and maintained may be advantageously used, in turn, in basic studies on liver function, investigations of the effects of hormones or drugs on hepatocytes, screening tests of drugs intended for treatment of hepatic diseases and so on. In addition, they are also useful as host cells in carcinogenicity test as well as in cultivation of hepatitis viruses in vitro. The invention provides such physiologically active substance with a potential usefulness.

The method for the preparation of the hHGF of the present invention will be illustrated in detail hereinunder.

The hHGF may be isolated efficiently with a high yield from human blood, particularly from the blood of the patient with fulminant hepatitis. The blood used herein as raw material can be obtained in a conventional manner and, usually, it may be advantageously available as serum or plasma. The blood derived from the patient with fulminant hepatitis is preferably the plasma available in plasma exchange therapy.

The preparation of the hHGF according to this invention from the above-specified raw material may be basically carried out in the same procedures, making use of the physical and chemical properties thereof, as commonly applied for the separation of proteinous substances from such biological materials as mentioned above. The procedures include, for example, treatment with usual precipitants for proteins, ultrafiltration, molecular sieve chromatography (gel filtration), centrifugation, electrophoresis, ion exchange chromatography, affinity chromatography, reversed phase chromatography, adsorption chromatography, dialysis, and their appropriate combinations.

A particularly desirable procedures for the preparation are as follows. The active substance may be prepared by ammonium sulfate precipitation in a fraction of approximately 1.1 to 2.1M from the raw material, e.g. plasma, that has been heated for about 15 minutes at ca. 56° C. The active substance may be further purified by, for example, gel filtration using an ordinary carrier and ion exchange chromatography with an anion exchanger such as DEAE. Furthermore, according to the studies of the present inventors, the hHGF provided by this invention has proved to show a high affinity for Affi-Gel Blue (Bio-Rad Laboratories, California, U.S.A.), heparin and hydroxyapatite, and hence chromatographies with these materials are most preferably used for its purification.

The above procedures may be performed in the same manner and under the same conditions as those in usual procedures in the art.

The hHGF thus purified and isolated may be identified with respect to the above-specified properties.

It has also been demonstrated that the hepatocyte-proliferating activity of the hHGF of the invention may be retained on treatment with sodium dodecylsulfate (SDS). Accordingly, SDS-polyacrylamide gel electrophoresis (SDS-PAGE) may be also preferably adopted as a means for the purification and isolation.

The present invention will be further illustrated by referring to the non-limitable Examples below.

EXAMPLE 1

Assay of HGF activity

Hepatic parenchymal cells were isolated from male rats of the Wistar strain (body weight: 200 g) using 0.05% collagenase (type I; Sigma-Aldrich Co., St. Louis, Mo., U.S.A.), according to the method described by Seglen (Methods in cell biology, Vol. 13, p.29, Academic Press, New York (1976)). The hepatic parenchymal cells were seeded in each well of 1.55 cm in diameter in a multi-well plastic dish (Nunc, Roskilde, Denmark) at a concentration of $5 \times 10^4$ cells/0.2 ml/cm$^2$ and incubated in monolayer culture in an atmosphere of 5% $CO_2$-95% air at 37° C. (Tanaka et al., J. Biochem. 84, 937-946 (1978)). The culture medium consisted of Williams E medium (Flow Laboratories, Virginia, U.S.A.) supplemented with 5% fetal calf serum (FCS: Filtron, Altona, Australia), 1 $\mu$M of dexamethasone, 100 U/ml of penicillin and 100 $\mu$g/ml of streptomycin, which is hereinafter referred to as "basal medium". The medium was replaced with the basal medium containing a test sample at 4 and 20 hours after the commencement of the incubation and then with the basal medium alone at 40 hours followed by the measurement of DNA synthesis.

The DNA synthesis was assayed by determining the amount of tritiated thymidine (Amersham Corp., Buckinghamshire, England) uptake by the cultured cells after 2 hours of incubation with $^3$H-thymidine at 4 $\mu$Ci/ml (2 Ci/mmol) at 37° C. Cultures to which hydroxyurea was added at a concentration of 10 mM was made as controls in the above assay. After the above labeling, the cells were washed three times with cold phosphate buffered saline (PBS), 2% perchloric acid and 95% ethanol. The cells were then allowed to dry in air, and solubilized with 0.8 ml of 2% SDS solution containing 2 mM ethylenediaminetetraacetic acid (EDTA) and 20 mM $NaHCO_3$. Aliquot of the resultant mixture was subjected to measurement of radioactivity and to protein assay. The protein assay was carried out according to the method of Lowry, using bovine serum albumin (BSA) as a standard. The amount of $^3$H-thymidine incorporated into the hepatic parenchymal cell DNA in the presence of the test sample was determined by subtracting therefrom the radioactivity count of the control, and converted to DNA synthesizing activity per $\mu$g of hepatocyte protein per hour (dpm/hr/$\mu$g protein) to represent the HGF activity of the test sample.

EXAMPLE 2

Preparation of hHGF

The plasma of the patient with fulminant hepatitis obtained in the plasma exchange therapy was used as a starting material for the preparation.

The plasma in an amount of 930 ml was heated for 15 minutes at 56° C. and subsequently centrifuged at 105,000 $\times$ g for 60 minutes at 4° C. The following operations for purification and isolation were all effected at a temperature of 4° C.

The resulting supernatant was diluted with an equal volume of distilled water and fractionated by precipitation using 3.8M ammonium sulfate (pH 6.0). The materials precipitated at 1.15 to 2.05M of ammonium sulfate concentration were dissolved in a small amount of PBS(−), and dialyzed against the same buffer.

The dialyzed fraction was then subjected to chromatography on an Affi-Gel Blue column (3.9 $\times$ 11 cm) equilibrated with PBS(−), and washed successively with 250 ml of PBS(−) and 250 ml of PBS(−) (pH 7.4) containing 1.4M NaCl. Fractions containing HGF activity were then eluted with 350 ml of 2M guanidine hydrochloride (pH 7.4). The eluate fractions were then pooled and dialyzed extensively against PBS(−) for 72 hours with at least five exchanges of PBS(−).

To the dialyzed sample, Triton X-100 was added at a final concentration of 0.013%; and the mixture was subjected to chromatography on a Heparin-Sepharose column (1.6 $\times$ 5 cm; Pharmacia, Uppsala, Sweden) equilibrated with PBs(−) containing 0.013% Triton X-100. After washing successively with 75 ml of the same PBS(−) and 50 ml of the same PBS(−) containing 0.5M NaCl, the active fractions were eluted with a linear gradient of 0.5-1.75M NaCl.

The active eluate fractions obtained at 0.84 to 1.15M NaCl were diluted twofold with PBS(−) containing 0.013% Triton X-100, and chromatographed on a hydroxyapatite column (1.6 $\times$ 5 cm; flow rate, 20 ml/hr; Bio-Rad Laboratories, California, U.S.A.) equilibrated with the same PBS(−). The column was washed with 20 ml of the same buffer and successively with 20 ml of 0.1M sodium phosphate buffer (pH 7.1) containing 0.15M NaCl and 0.013% Triton X-100 followed by elution with a 0.1-0.5M sodium phosphate linear gradient at room temperature. The eluate was fractionated in 2 ml.

The typical elution pattern by this procedure is shown in FIG. 1, in which the HGF activity (curve (1)) and sodium phosphate concentration (curve (2)) are plotted as ordinate against the fraction number as abscissa. Fractions with peak activity (Nos. 60 to 66) were pooled and stored at −20° C.

Thus, the hHGF preparation with purity of more than 200,000-fold over the starting plasma material was obtained.

The hHGF preparation was inactivated, in respect of its HGF activity, by heating (for 10 minutes at 80° C.) or by enzymatic treatment (with 0.1 mg/ml of trypsin for 30 minutes at 37° C. or 0.1 mg/ml of chymotrypsin for 30 minutes at 37° C.). It proved to be stable on incubation (for 20 hours at 4° C.) in any of the following solutions tested: 0.5M acetic acid, 0.1M acetate buffer (pH 4.0), the same buffer (pH 5.0), 0.1M phosphate buffer (pH 7.4) and 0.1M glycine buffer (pH 9.5).

EXAMPLE 3

SDS-PAGE of hHGF preparation

SDS-PAGE was effected at room temperature in 8% separating gel (1 mm in thickness) with a 3% stacking gel according to the method of Laemmli (Nature, 227, 680-685 (1970)).

The hHGF preparation obtained in Example 2 above was concentrated approximately ten-fold with Centricon 10 (Amicon Corp., Massachusetts, U.S.A.). The concentrated hHGF was combined with an equal volume of a double-strength sample buffer consisted of 125 mM tris-HCl buffer, pH 6.8, containing 6% SDS, 20% glycerol and 0.025% bromophenol blue, and the mixture was incubated for 1 hour at 25° C. to serve as a sample for electrophoresis. After electrophoresis, three lanes of separating gel were sliced in 1.5 mm width using a razor blade. Each slice was placed in a test tube, minced, and incubated for extraction with 1 ml of PBS(−) containing 0.013% Triton X-100 and 0.02% SDS with a constant stirring for 20 hours at room temperature. The extract was subjected to HGF activity assay. Another lane of separating gel was fixed with 10% trichloroacetic acid solution and silver-stained to estimate the molecular weight of the hHGF by reference to molecular weight standards (Pharmacia, Uppsala, Sweden).

Figure 2:
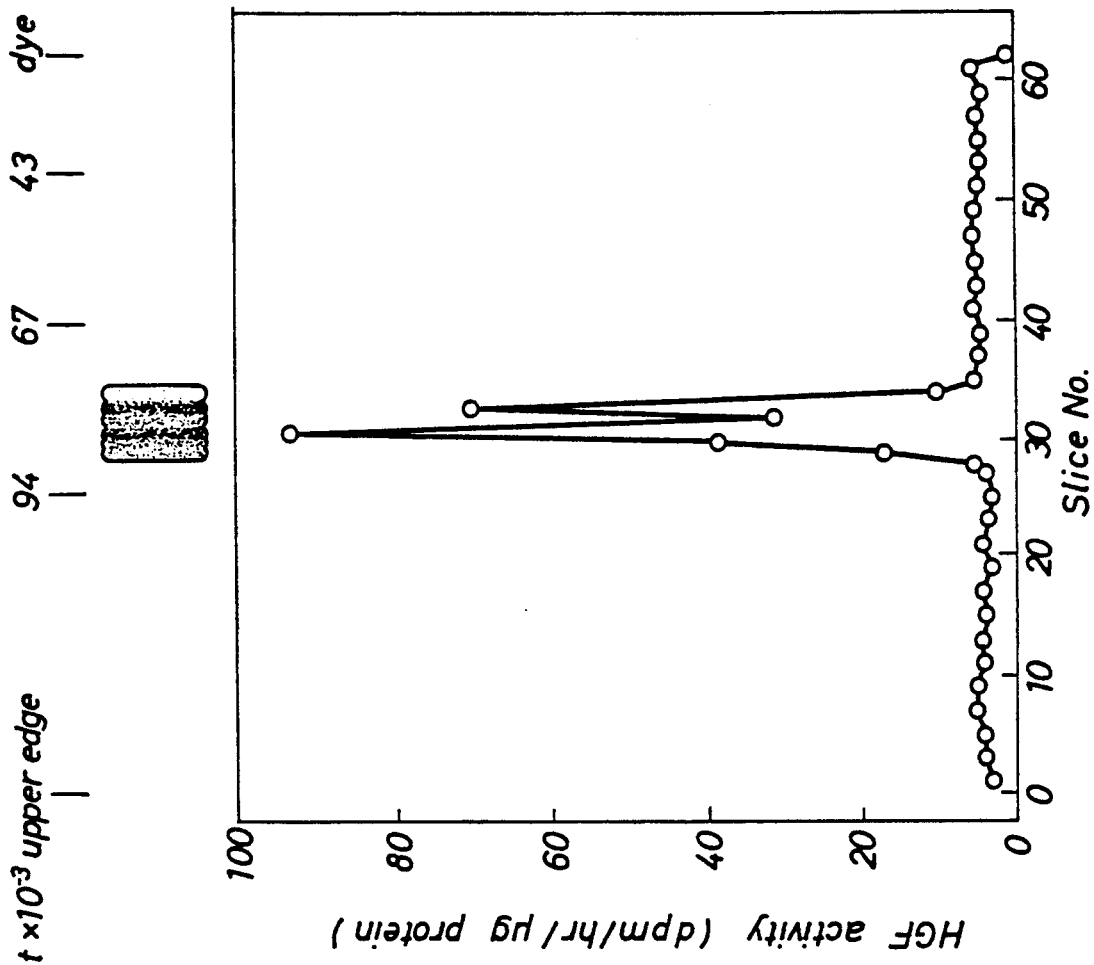
FIGS. 2 and 3 illustrate the results of SDS-PAGE analysis of the hHGF of the invention.

The results obtained are presented in FIG. 2, where the abscissa represents the slice number and the ordinate the HGF activity.

The SDS-PAGE data indicated in FIG. 2 show that, hHGF provided by this invention migrated as a band ranging in molecular weight from approximately 76,000 to 92,000 under non-reductive condition and that the HGF activity was found in the same slice numbers as the band (slice Nos. 29 to 34)

The hHGF extracts from gel slices described in the above were independently subjected to SDS-PAGE in the same manner as in the above.

Figure 3:
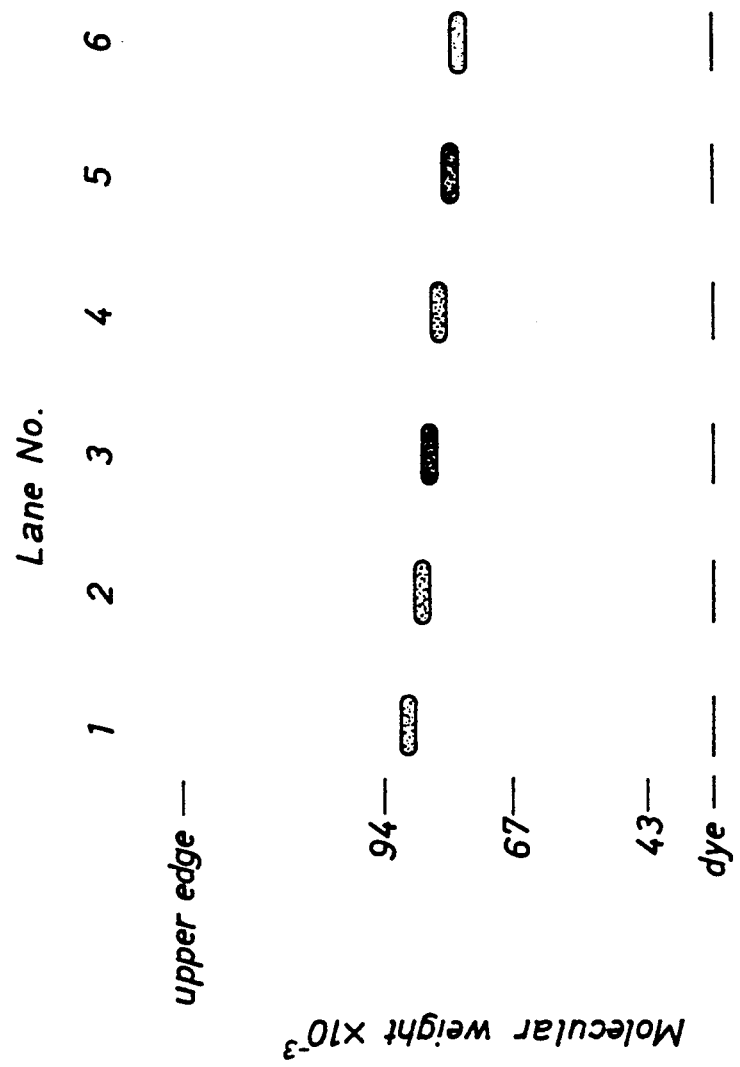

The results of the analysis are shown in FIG. 3. In FIG. 3, the abscissa represents the lane number: Lane 1 shows a band from slice No. 29 in the above; Lane 2, slice No. 30; Lane 3, slice No. 31; Lane 4, slice No. 32; Lane 5, slice No. 33; and Lane 6, slice No. 34, respectively. The ordinate represents the molecular weight ($\times 10^{-3}$) estimated by molecular weight standards.

The above-described data in FIG. 3 indicated there is a little diversity in molecular weight of the hHGF which could be isolated by the method described above. The molecular weights of the isolated hHGFs, along with their HGF activities, are shown in Table 1. The HGF activity was parallel to the intensity of stain.

SDS-PAGE of the sample under reductive condition has revealed main bands at molecular weights of 56,000–65,000 and 32,000–35,000, suggesting that hHGF is a proteinous substance consisted of these materials with different molecular weights bound with each other by disulfide bonds and that the above-described seven molecular forms are essentially identical as hHGF.

TABLE 1

| Lane No. | Molecular weight (Non-reductive condition) | HGF activity (dpm/hr/μg protein) |
|---|---|---|
| 1 | ca. 92,000 | 17.3 |
| 2 | ca. 88,000 | 38.6 |
| 3 | ca. 86,000 | 93.9 |
| 4 | ca. 83,000 & ca. 81,000 | 31.2 |
| 5 | ca. 79,000 | 70.5 |
| 6 | ca. 79,000 & ca. 76,000 | 10.5 |

EXAMPLE 4

Dose-dependency of hHGF activity

Tests were effected to check dose-dependency of HGF activity, using the hHGF preparation obtained in Example 3 above.

Figure 4:
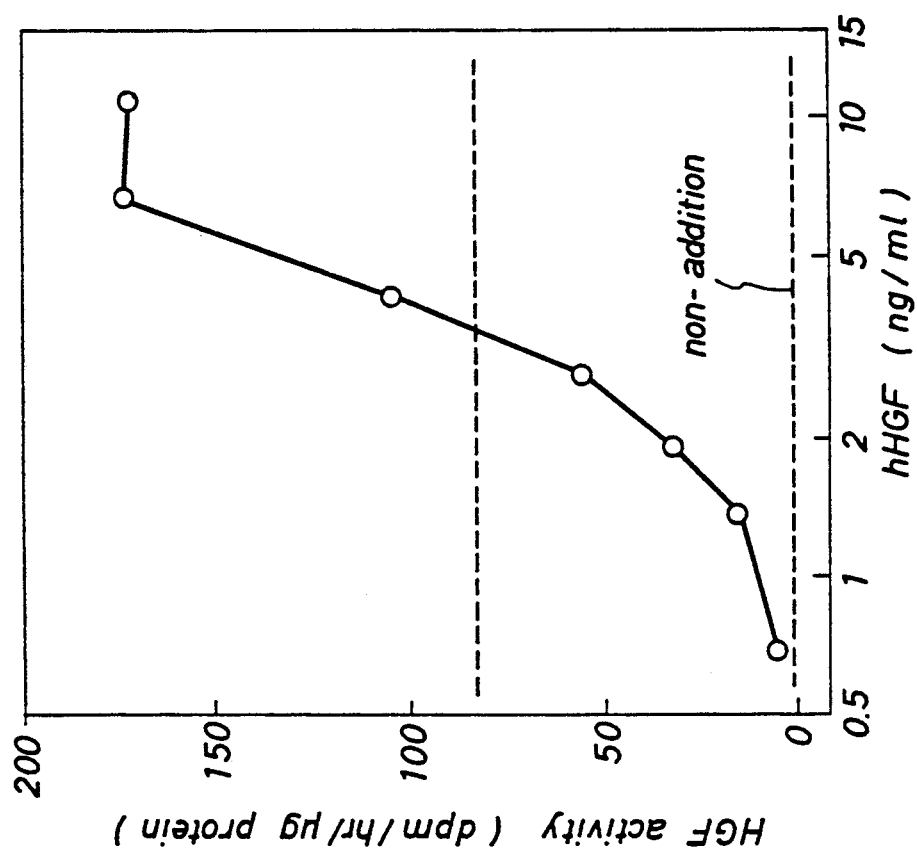
FIG. 4 illustrate a dose-dependent activity curve of the hHGF of the invention.

FIG. 4 illustrates the results of the tests, where the HGF activity (dpm/hr/μg protein) is plotted as ordinate against the concentration of hHGF (ng/ml) as abscissa. As a reference, HGF activity shown by murine epithelial growth factor "mEGF" (Wako Pure Chemical Industries, Ltd.) at a concentration of 25 ng/ml was represented by dotted line.

EXAMPLE 5

HGF activity

Tests were also effected to confirm the HGF activity of the hHGF obtained in Example 2 above as well as insulin, murine epithelial growth factor (mEGF; Wako Pure Chemical Industries, Ltd.) and human epithelial growth factor (hEGF; Wakunaga Pharmaceutical Co., Ltd.) and combinations thereof.

The results of the tests are presented in Table 2.

The labeling index shown in Table 2 was calculated from enumeration of $^3$H-thymidine-labeled cell nuclei on autoradiography of cultures of at least 250 cells (Biomed. Res. 6, 231 (1985)) and expressed as a percentage. This index reflects the degree of proliferation of hepatic parenchymal cells. The data on HGF activity and labeling index are given as mean value ± standard deviation (SD) or as mean value (in duplicate and triplicate determinations).

TABLE 2

| Test sample | Concentration (ng/ml) | HGF activity (dpm/hr/μg protein) | Labeling index (%) |
|---|---|---|---|
| None | — | 1.7 ± 0.4 | <0.2 |
| Insulin | 600 | 7.8 ± 0.8 | 4.1 |
| hEGF | 2.1 | 42.7 ± 3.3 | 9.2 |
|  | 6.3 | 175.4 ± 3.3 | 24.7 ± 7.7 |
|  | 9.4 | 197.9 ± 3.1 | 31.7 ± 3.4 |
| hHGF | 8.3 | 297.9 ± 19.4 | 50.1 ± 1.2 |
| hHGF + hEGF | 8.3 + 6.3 | 578.9 ± 47.2 | 66.8 |
|  | 8.3 + 9.4 | 569.1 ± 3.2 | 64.0 |
| Insulin + mEGF | 600 + 50 | 461.8 ± 35.3 | — |
| Insulin + hEGF | 600 + 6.3 | 503.9 ± 6.5 | 63.1 ± 5.6 |
| Insulin + hHGF | 600 + 8.3 | 461.5 ± 21.6 | 77.9 ± 5.3 |
| Insulin + hHGF + mHGF | 600 + 8.3 + 6.3 | 684.0 ± 41.0 | 85.0 ± 4.0 |

It is obvious from Table 2 that hHGF has a higher HGF activity than insulin, mEGF and hEGF, and that the additional and synergistic effects may be observed in the combinations of the hHGF with the others.

The HGF activity of the hHGF was also confirmed by observation of karyokinesis of hepatic parenchymal cells as well as increase of a total count of nuclei in culture wells under the phase-contrast microscope.

What is claimed is:

1. A substantially purified and isolated human hepatocyte growth factor, comprising a proteinaceous substance which exhibits the following physicochemical properties and physiological activity:
   i) having a molecular weight which is estimated to be approximately 76,000–92,000 by SDS-PAGE analysis, under non-reductive conditions;
   (ii) having HGF activity;
   (iii) said HGF activity being inactivated by heat treatment for 10 minutes at 80° C.;
   (iv) said HGF activity being lost by digestion with trypsin or with chymotrypsin; and
   (v) having such a high affinity for heparin that when adsorbed by Heparin-Sepharose column, said growth factor is not eluted therefrom below 0.8M NaCl in a PBS(−) buffer at pH 7.4 containing 0.013% Triton X-100.

2. The human hepatocyte growth factor according to claim 1, which is derived from human blood of patients with fulminant hepatitis.

3. The human, hepatocyte growth factor according to claim 1, which is stable on incubation for 20 hours at 4° C. in 0.1M acetate buffer at pH 5.0.

* * * * *